United States Patent
Graumann et al.

(10) Patent No.: US 8,784,794 B2
(45) Date of Patent: *Jul. 22, 2014

(54) LONG-TERM STORAGE OF NON-GLYCOSYLATED RECOMBINANT HUMAN G-CSF

(75) Inventors: Klaus Graumann, Schwaz (AT); Helmut Lerch, Stans (AT); Thomas Lauber, Kufstein (AT)

(73) Assignee: Sandoz AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/805,180

(22) PCT Filed: Jun. 22, 2011

(86) PCT No.: PCT/EP2011/060454
§ 371 (c)(1),
(2), (4) Date: Feb. 22, 2013

(87) PCT Pub. No.: WO2011/161165
PCT Pub. Date: Dec. 29, 2011

(65) Prior Publication Data
US 2013/0164253 A1  Jun. 27, 2013

Related U.S. Application Data

(60) Provisional application No. 61/360,562, filed on Jul. 1, 2010.

(30) Foreign Application Priority Data

Jun. 22, 2010 (EP) ..................................... 10166915

(51) Int. Cl.
*A61K 9/19* (2006.01)
(52) U.S. Cl.
USPC ........................................ 424/85.1; 530/399
(58) Field of Classification Search
None
See application file for complete search history.

(56) References Cited

U.S. PATENT DOCUMENTS 6,956,023 B1  10/2005  Calhoun et al.

FOREIGN PATENT DOCUMENTS

| DE | 3723781 A1 | 1/1988 |
| EP | 0373679 | 6/1990 |
| EP | 0456200 | 11/1991 |
| EP | 1197221 | 4/2002 |
| WO | WO2005039630 A2 | 5/2005 |
| WO | WO2005042024 A1 | 5/2005 |
| WO | WO2007034509 A2 | 3/2007 |
| WO | WO2007099145 A1 | 9/2007 |
| WO | WO2008122415 A1 | 10/2008 |
| WO | WO2009027076 A1 | 3/2009 |

OTHER PUBLICATIONS

"Characterization, Formulation, and Stability of Neupogen (Filgrastim), a Recombinant Human Granulocyte-Colony Stimulating Factor," Alan C. Herman, et. al, Analytical Research and Development, Amgen, Inc. pp. 303-328, 1996.
"Formulation of Neulasta (pegfilgrastim)," Deirdre Murphy Piedmonte, Michael J. Treuheit, ScienceDirect, pp. 50-58, Advanced Drug Delivery Reviews vol. 60 (2008).

*Primary Examiner* — Brian J Gangle
*Assistant Examiner* — Andrea McCollum
(74) *Attorney, Agent, or Firm* — Luedeka Neely Group, P.C.; J. David Gonce, Esq.

(57) ABSTRACT

The present invention provides a method for stable long-term storage of non-glycosylated recombinant human Granulocyte-Colony Stimulating Factor ("G-CSF"), wherein an aqueous acetate or glutamate buffered G-CSF composition containing the non-glycosylated recombinant human G-CSF and sorbital is cooled to a temperature of −15° C. or below to obtain a frozen G-CSF composition, which frozen composition is then stored in the frozen state and then increased in temperature to a temperature within the range of from 2° C. to 8° C. for a period of time adjusted to allow the composition to thaw and to obtain a liquid composition having a G-CSF content of at least 95% of the G-CSF content of the original composition.

13 Claims, 1 Drawing Sheet

Isoelectric Focussing of Glutamate-buffered G-CSF compositions after Storage for 2 Months at -20 °C and 25 °C

LONG-TERM STORAGE OF NON-GLYCOSYLATED RECOMBINANT HUMAN G-CSF

This application is a national phase entry of PCT International application number PCT/EP2011/060454, filed Jun. 22, 2011. This applications also claims the benefit of the earlier filing dates of European application EP 10166915.8, filed Jun. 22, 2010, and US provisional application 61/360,562, filed Jul. 1, 2010.

FIELD OF THE INVENTION

The present invention relates to a method for long-term storage of non-glycosylated recombinant human G-CSF.

BACKGROUND OF THE INVENTION

G-CSF (Granulocyte-Colony Stimulating Factor) is a naturally occurring growth factor which belongs to the family of cytokines. G-CSF plays a crucial role in hematopoesis and enhances maturation, proliferation, differentiation and survival of neutrophils and neutrophilic successor cells. Clinically, G-CSF is mainly used for controlling tumors and, in particular, for the treatment of neutropenia following chemotherapy, and it is also applied for bone marrow transplantations and in the treatment of infectious diseases.

Human G-CSF in its naturally occurring form is an about 20 kDa glycoprotein which has five cysteine residues. Four of these residues form two intramolecular disulfide bridges which are crucial for the activity of the protein. As G-CSF is obtained only in small amounts from natural sources, mainly recombinant forms of G-CSF are used in medicaments, in particular those which have been produced by expressing the protein in prokaryotic hosts. Proteins expressed in prokaryotic hosts such as *E. coli* differ from natural occurring G-CSF in that they are not glycosylated. Proteins expressed in *E. coli* have an additional N-terminal methionine residue necessary for expression in this host organism.

Due to the high hydrophobicity of the protein, non-glycosylated recombinant G-CSF is relatively unstable. The molecule easily adsorbs to the inner surface of storage vessels, vials, syringes or the like and forms dimers and higher aggregates. Conventional liquid G-CSF formulations also are sensitive to mechanical stress, for example as a result of shaking during transport, and to accidental freezing and thawing, which may also result in higher levels of aggregates and loss of biological activity. Moreover, G-CSF is subject to chemical modifications such as deamidation, oxidation, cleavage of disulfide bridges or proteolysis. Deamidation, which occurs more rapidly than other degradation routes, is a particular problem due to the high glutamine content of G-CSF. Altogether, this may result in a reduced content of biologically available and active monomeric G-CSF, particularly upon prolonged storage of the protein. This is not only costly but also is undesirable for therapeutic reasons, for example if the G-CSF is to be administered over a prolonged period of time at a constant dosage. Furthermore, products formed by multimerization or deamidation may result in an undesired immune response.

Stabilization of G-CSF formulations is subject of various patent and non-patent literature.

DE-A-37 23 781 describes aqueous phosphate-buffered G-CSF formulations containing pharmaceutically acceptable surfactants such as polyoxyethylene sorbitan esters which are used in combination with human serum albumin and mannitol for stabilizing the active ingredient. These formulations are stable at 4° C. over a prolonged period of time. Due to their antigenic properties, however, proteins and peptides of human and animal origin may cause undesired immunological reactions.

EP-A-0 373 679 discloses G-CSF formulations having a pH value of from 2.75 to 4.0 and low conductivity, which may be stored over prolonged periods of time without formation of aggregates. If any, buffer is used in these formulations in small amounts of less than 2 mM in order to avoid the aggregation of G-CSF.

EP-A-1 197 221 discloses long-term stable G-CSF formulations at a pH of from 5 to 7, which contain one or more amino acids of the group of lysine, histidine, arginine, aspartic acid, glutamic acid, threonine and asparagine, as well as one or more hydrophobic amino acids. Methionine is added to prevent oxidation of methionine residues in the G-CSF molecule.

WO-A-2007/034509 discloses stable aqueous formulations containing recombinant human G-CSF and an amino acid which is an oxidation suppressant for the methionine residues in the protein.

WO-A-2005/042024 discloses pharmaceutical compositions comprising G-CSF and an acid such as acetic acid or glutamic acid, which is free of surfactants.

WO-A-2005/039620 discloses succinate- and tartrate-buffered compositions stable over a wide pH range.

Herman, A. C. et al. ("Characterisation, Formulation, and Stability of Neupogen® (Filgrastim), a Recombinant Human Granulocyte-Colony Stimulating Factor." In: Formulation Characterisation and Stability of Protein Drugs, pp. 303-328, R. Pearlman and Y. J. Wang, Eds., Plenum Press, New York, 1996) describe stabilized compositions of non-glycosylated recombinant G-CSF which contain 10 mM of sodium acetate, pH 4.0, 5% of mannitol and 0.004% of Polysorbate 80. Such compositions are stable for more than 24 months at 2-8° C. Substituting mannitol with sorbitol in a filgrastim formulation was found to eliminate sensitivity of the protein to aggregation during inadvertent freezing and thawing. Storing in a freezer, however, is to be avoided according to the manufacturer's instructions.

WO-A-2007/099145 discloses liquid acetate-buffered G-CSF formulations comprising polysorbate 20 and/or polysorbate 80 as a surfactant and having a pH-value between 4.1 and 4.4

WO-A-2008/122415 discloses liquid aqueous glutamate-buffered G-CSF formulations having a pH of from 3.5 to 4.8 which are stable under conditions of mechanical stress encountered, for example, upon freezing and thawing.

OBJECTS AND SUMMARY OF THE INVENTION

Piedmonte et al. (Pharmaceutical Research, Vol. 24, No. 1, January 2007, pp: 136-146) describe the effect of sorbitol on protein aggregation in frozen protein formulations.

The object of the present invention was to provide a method for stable long-term storage of biologically active non-glycosylated recombinant human G-CSF, wherein degradation, in particular deamidation, and loss of G-CSF during storage due to adsorption phenomena to container walls is reduced.

This object is achieved by the method of the present invention for stable long-term storage of non-glycosylated recombinant human G-CSF, said method comprising the steps of:
  (a) providing an aqueous acetate or glutamate buffered G-CSF composition containing the non-glycosylated recombinant human G-CSF and sorbitol;

(b) cooling the G-CSF composition provided in step (a) to a temperature of −15° C. or below to obtain a frozen G-CSF composition;
(c) storing the G-CSF composition obtained in step (b) in the frozen state; and
(d) increasing the temperature of the frozen G-CSF composition of step (c) to a temperature within the range of from 2° C. to 8° C. over a period of time adjusted to allow the composition to thaw and to obtain a liquid composition having a G-CSF content of at least 95% of the G-CSF content of the composition provided in step (a).

The present invention further relates to a method of providing a pharmaceutical composition of non-glycosylated recombinant human G-CSF, said method comprising the steps of:
(a) formulating the non-glycosylated recombinant human G-CSF with an acetate or glutamate buffer and sorbitol to obtain an aqueous buffered G-CSF composition;
(b) cooling the G-CSF composition of step (a) to a temperature of −15° C. or below to obtain a frozen G-CSF composition;
(c) storing the G-CSF composition obtained in step (b) in the frozen state;
(d) increasing the temperature of the frozen G-CSF composition of step (c) to a temperature within the range of from 2° C. to 8° C. over a period of time adjusted to allow the composition to thaw and to obtain a liquid composition having a G-CSF content of at least 95% of the G-CSF content of the composition provided in step (a); and
(e) filling the liquid composition obtained in step (d) into primary packagings for parenteral use.

In the course of the invention it has been found that by the method of the invention deamidation and loss of non-glycosylated recombinant human G-CSF can considerably be reduced or even avoided, even if the G-CSF is provided in high concentrations and in large volumes and without the use of surfactants. In this way, activity is maintained even at prolonged storage. Moreover, as G-CSF compositions can be stored in the frozen state, they are not sensitive to mechanical stress as may be experienced, for example, during transport.

BRIEF DESCRIPTION OF THE DRAWING

FIG. 1 shows a comparison of deamidation products observed with filgrastim samples subjected to the method of the invention (lanes 1 and 2) and filgrastim samples stored at a temperature of 25° C. (lanes 3 and 4) as determined by Isoelectric Focussing (IEF).

DETAILED DESCRIPTION OF THE INVENTION

The non-glycosylated recombinant human G-CSF protein used in the compositions of the present invention (in the following also referred to as G-CSF) may be any protein comprising the non-glycosylated amino acid sequence of human G-CSF and having the biological activity thereof. Non-glycosylated recombinant human G-CSF is typically obtained by expressing the human G-CSF gene in a prokaryotic host such as *E. coli*. Non-glycosylated recombinant human G-CSF expressed in *E. coli* typically has an N-terminal Met residue. In a preferred embodiment of the invention, the human G-CSF comprises or has the primary structure of human G-CSF plus an N-terminal methionine (r-met HU G-CSF) as indicated in the European Pharmacopoeia 6.3 Monograph (01/2009:2206; "Filgrastim Concentrated Solution" page 4142) or in Herman, A. C. et al. (supra), i.e., the amino acid sequence of filgrastim, or is a variant thereof having essentially the biological activity of filgrastim, for example a variant having N-terminal or C-terminal extensions such as fusion proteins, a variant wherein the methionine residue at the N-terminal end has been replaced by some other amino acid such as glycine, or a variant having neutral mutations in the amino acid sequence. G-CSF variants useful in the formulations of the present invention are disclosed, e.g., in EP-A-0 456 200.

The buffer system used in the G-CSF compositions of the present invention is an acetic acid/acetate buffer or a glutamic acid/glutamate buffer. The composition used in the invention is preferably free of other buffering agents. The buffers used according to the invention can be prepared, for example, starting from acetic acid or glutamic acid and/or a salt thereof and adjusting the pH to the desired value using the corresponding acid or base or another suitable inorganic or organic acid or inorganic base such as hydrochloric acid or an alkali hydroxide or alkaline earth hydroxide. Physiologically acceptable acetic acid salts or glutamic acid salts are preferred, e.g., alkali, alkaline earth, or ammonium salts. Alkali or ammonium salts are preferred, in particular the monosodium salt. Preferably, the buffer is prepared starting from acetic acid or glutamic acid and the pH value is adjusted using a suitable inorganic base, for example sodium hydroxide.

The pH value of the composition provided in step (a) of the process of the invention is typically in the range of from 3.5 to 5.0, preferably in the range of from 3.7 to 4.8. More preferably the pH is in the range of from 3.7 to 4.6, for example of from 4.0 to 4.6.

The concentration of the acetate or glutamate buffer is advantageously adjusted so as to achieve a pH-stabilizing effect at the desired pH value and a sufficient buffer capacity. Usually, the acetate or glutamate buffer has a concentration of at least 0.5 mM, preferably of from 1 to 100 mM, and more preferably of from 2 to 80 mM. Buffer concentrations in the range of from 2 to 40 mM, in particular of from 2 to 25 mM, for example of from 5 to 15 mM and preferably about 10 mM, will provide sufficient stability and will be low enough to avoid undesired tissue reactions upon injection of the composition.

The G-CSF concentration in the composition provided in step (a) of the method of the invention will depend on the intended use. The upper concentration limit results from the solubility of G-CSF in the buffer. Typically, the G-CSF concentration is in a range of from 0.1 to 8 mg/ml, preferably of from 0.25 to 6.5 mg/ml. In analytical samples or in pharmaceutical compositions to be administered without further dilution, G-CSF is present in an amount which typically is in a range of from 0.1 to 2.0 mg/ml, preferably up to 2.5 mg/ml. In more concentrated compositions, for example compositions containing G-CSF as a process intermediate, which may be further processed to obtain the drug product suitable for administration to a patient, the G-CSF concentration typically is in a range of from 2.5 mg/ml to 8.0 mg/ml, preferably of from 2.5 to 6.5 mg/ml, and more preferably up to 5.5 mg/ml.

The composition provided in step (a) of the method of the invention comprises sorbitol as a tonicity modifier. Preferably, sorbitol is the only tonicity modifier used in the composition except for the buffer system. Sorbitol is typically present in an amount of up to 200 mg/ml, preferably of from 10 to 100 mg/ml, more preferably of from 25 to 75 mg/ml, for example about 50 mg/ml.

The compositions used in the method of the invention may or may not comprise a surfactant. If a surfactant is present, the surfactant typically is a non-ionic surfactant. Preferably, the non-ionic surfactant is selected from the group consisting of fatty alcohol ethoxylates, alkylpolyglycosides, polyoxyalkylenes, polysorbates or mixtures of two or more thereof. Polyoxyalkylenes such as polyoxyalkylene block copolymers, for example Poloxamer 188 (available under the trade name PLURONIC F68), and polysorbates, i.e., polyoxyethylene sorbitan esters of aliphatic fatty acids are preferred. Most preferred are polysorbates such as polyoxyethylene sorbitan monolaurate (available under the trade name TWEEN 20), polyoxyethylene sorbitan monopalmitate (TWEEN 40), polyoxyethylene sorbitan monostearate (TWEEN 60), polyoxyethylene sorbitan tristearate (TWEEN 65), polyoxyethylene-sorbitan monooleate (TWEEN 80) and polyoxyethylene sorbitan trioleate (TWEEN 85). Polyoxyethylene sorbitan monolaurate and polyoxyethylene sorbitan monooleate are most preferred.

If a surfactant is used, the surfactant is preferably present in an amount of 5 mg/ml or less, preferably 1 mg/ml or less. Preferably, surfactants, in particular polysorbates, are used in amounts of from 0.001 to 1.0 mg/ml, more preferably of from 0.01 to 0.5 mg/ml.

While the composition provided in step (a) of the method of the invention may comprise further agents such as amino acids, reducing agents, antioxidants and serum proteins, the composition typically consists of G-CSF, the aqueous acetate or glutamate buffer, sorbitol and, optionally, a surfactant, and thus is free of other agents.

The compositions provided in step (a) of the method of the invention may be prepared in a manner known per se. For example, the buffer substances, i.e., acetic acid or glutamic acid or a salt thereof, the sorbitol and, optionally, other additives such as surfactants are dissolved in a suitable amount of an aqueous solvent, usually water. If necessary, the pH value is adjusted using a suitable acid or base as described above. Following sterilization, for example by filtration through a sterile filter, G-CSF is added in the desired concentration. Alternatively and preferably, the G-CSF composition used in step (a) is obtained as a batch from the production process with or without re-buffering.

The aqueous G-CSF composition provided in step (a) of the method of the invention can be provided in any desired volume but preferably has a volume in the range of from 0.1 ml to 8 l, preferably of from 5 ml to 4 l, more preferably of from 10 ml to 2.0 l, and most preferably of from 100 ml to 1.5 l. The composition is provided in a suitable container such as a polyethylene (PE) bag, a glass bottle, or a bottle made of polyethylene terephthalate (PET) without or with glycol (PETG).

Filling the composition into the container is typically carried out under sterile conditions and preferably using an inert gas such as nitrogen. Typically, containers are filled only partially with the composition and preferably up to a volume of not more than 90%, the headspace in the containers being preferably filled with the inert gas.

The liquid aqueous G-CSF composition of the present invention provided in the desired volume is cooled down to a temperature of −15° C. or below until frozen. Typically, the compositions are cooled to a temperature of between −15 and −25° C., for example about −20° C., or they are cooled to a temperature of between −60° C. and −80° C. Cooling can be effected, for example, in a freezer or a cold room or by submerging the containers with the G-CSF composition into liquid nitrogen.

The frozen G-CSF composition obtained in step (b) is stored in the frozen state at the desired temperature of −15° C. or below. Typically, the composition is stored at the temperature to which the composition has been cooled, i.e., as described above, preferably at a temperature of between −15 and −25° C. or between −60 and −80° C., which is the temperature standard cold rooms or deep freezers are defined to. Typically, the frozen G-CSF composition is stored over a period of at least two days, preferably at least one month, for example for at least three months or at least six months. It has been found that deamidation is considerably reduced during the time period where the G-CSF composition is stored in the frozen state (see Example 4 and FIG. 1).

Following storing of the frozen G-CSF composition in step (c), the temperature of the frozen composition is increased to a temperature within the range of from 2° C. to 8° C. over a period of time adjusted to allow the composition to thaw and to obtain a liquid composition having a G-CSF content of at least 95% of the G-CSF content of the composition provided in step (a).

The term "increasing the temperature to a temperature within the range of from 2° C. to 8° C." means that the composition is not exposed to a temperature above 8° C. Specifically, according to one embodiment of the invention, the frozen compositions can be warmed to a temperature between 2° C. and 8° C. by gradually or linearly increasing the temperature over an extended period of time. The extended period of time necessary to thaw the frozen composition and to obtain a liquid composition having a G-CSF content which is at least 95% of the G-CSF content of the composition originally provided is typically at least 6 hs. For example, in case a composition is kept in the frozen state at a temperature of −20° C., the composition can be warmed from −20° C. to +4° C. over a period of 6 hs with a gradual or linear hourly temperature increase of 4° C. A linear temperature gradient can be run, for example, using the Integrated Biosystems CryoPilot™ System.

According to a preferred embodiment of the invention, the frozen composition will be immediately transferred to the desired temperature between 2° C. and 8° C. and will then be maintained at that temperature for an extended period of time to allow the frozen composition to thaw and to obtain a liquid composition having the required G-CSF content. Typically, the frozen composition is transferred to a cold room or a water bath adjusted to this temperature range. In this case, the period of time for which the composition is maintained at that temperature depends, e.g., on the volume of the frozen G-CSF composition and the concentration of G-CSF in the composition. As a rule, the period of time required for a composition having a large volume, e.g., 100 ml or more, and a high G-CSF concentration is longer than for a composition having a small volume, e.g., below 100 ml, and a low G-CSF concentration. Likewise, the period of time required in a cold room is longer than in a water bath. Generally, the time period required to obtain the desired high G-CSF content is at least 12 hours and typically the time period is in the range of from 12 to 72 hours. For example, the time required for a composition having a small volume of below 100 ml generally is in the range of from 12 to 24 hours, while the time required for a composition having a large volume of 100 ml or more, for example of from 100 ml to 8 l, such as 0.8 l, and/or a high concentration of G-CSF, for example of from 2.5 to 8 mg/ml, is typically 18 hours or more, for example 24 to 48 hours in a water bath and 36 hours or more, for example 36 to 72 hours, in a cold room. Still larger volumes may require proportionally longer times.

In the liquid compositions obtained, the G-CSF content is at least 95%, preferably at least 97%, and most preferably at least 99%, of the G-CSF content of the composition provided in step (a). The term "G-CSF-content" is meant to encompass monomeric G-CSF and multimers thereof as well as related proteins derived therefrom such as deamidated and oxidized variants. The G-CSF-content can be determined, for example, by Size Exclusion Chromatography (SEC) or by Reversed Phase-HPLC (RP-HPLC) as described in the European Pharmacopoeia 6.3 Monograph (01/2009:2206; "Filgrastim Concentrated Solution" pages 4143-4144, in particular page 4143: "Impurities with molecular masses higher than that of filgrastim. Size-exclusion chromatography (2.2.30)" and "Related proteins. Liquid chromatography (2.2.29)"). While both methods give the same results, typically RP-HPLC is used.

Using the method of the invention, the biological potency of the recombinant G-CSF obtained in step (d) is essentially maintained. Specifically, the biological potency is at least 90%, preferably at least 95%, and more preferably at least 97%, 98% or 99% relative to the biological potency of the G-CSF provided in step (a). Biological activity is determined as described for filgrastim in the European Pharmacopoeia 6.3 Monograph (01/2009:2206; "Filgrastim Concentrated Solution"; pages 4142-4144, in particular page 4144: ASSAY—"Potency"). In brief, biological potency of the composition obtained in step (d) is determined by measuring its ability to stimulate proliferation of NFS-60 cells compared with the composition provided in step (a) calibrated in International Units as a reference. To determine the number of viable cells, intracellular ATP may be quantified using a luciferase chemiluminescence system. The measured luminescent signal is proportional to the amount of ATP which is directly proportional to the number of cells present. Relative potency may be calculated using a suitable statistical method, for example the parallel line assay according to European Pharmacopoeia 5.3 Monograph, and is expressed in percent of the composition obtained in step (d) compared to the composition of step (a).

Following step (d), in particular in the method of providing a pharmaceutical composition of non-glycosylated recombinant human G-CSF, the obtained liquid composition may be filled into primary packagings for parenteral use such as vials or syringes. Advantageously, the liquid composition may be divided into aliquots suitable for administration to a patient, for example, by injection or infusion, before filling. Concentrated solutions of G-CSF may be diluted before filling, and, optionally, the dilution buffer may also contain surfactant and other additives.

The G-CSF formulations obtained after storing and thawing in steps (c) and (d) of the method of the invention show no or only a minor loss of G-CSF protein due to adsorption, deamidation or aggregation of the protein. As described above, the G-CSF composition finally obtained according to the method of the invention has an overall G-CSF content of at least 95% of the initial content of G-CSF. These compositions, optionally after dilution, may be used as pharmaceuticals in various application forms, for example preparations for injection or infusion, in particular for intravenous, intramuscular, or subcutaneous administration. The pharmaceuticals obtained may be used for any indication for which G-CSF may be employed, such as for the treatment of neutropenia, for bone marrow transplantations, and in the treatment of infectious diseases and of tumor diseases.

The present invention will now be illustrated in more detail with reference to the following examples and to FIG. 1, which are not intended to limit the invention.

EXAMPLES

Methods

1. Size Exclusion Chromatography (SEC)

Aggregation analysis by SEC was performed according to the method described in the European Pharmacopoeia 6.3 Monograph (01/2009:2206; "Filgrastim Concentrated Solution" page 4143: "Impurities with molecular masses higher than that of filgrastim. Size-exclusion chromatography (2.2.30)") except that fluorescence detection was used. Briefly, hydrophilic silica gel was used as a stationary phase at a temperature of 30° C. Elution was carried out using a phosphate buffered ammonium hydrogen carbonate solution as a mobile phase at a flow rate of 0.5 ml/min. Fluorescence detection was at 345 nm and excitation was at 280 nm. The chromatograms were quantified, differentiating G-CSF monomers from higher aggregates as impurities. Results of experiments are expressed as percent peak area (%).

2. Reversed Phase (RP) HPLC

G-CSF content and impurities (deamidated and oxidized variants) in samples after long term storage using RP-HPLC were determined according to the method described in the European Pharmacopoeia 6.3 Monograph (01/2009:2206; "Filgrastim Concentrated Solution", page 4143: "Related proteins. Liquid chromatography (2.2.29)") except that fluorescence detection was used for determination of purity as described above. Protein content was determined against a G-CSF reference standard by UV detection at 215 nm. Results of experiments are expressed as percent peak area (%).

3. Isoelectric Focussing (IEF)

Analysis of samples after freezing and thawing for impurities with charges differing from that of filgrastim was carried out by IEF according to the method described in the European Pharmacopoeia 6.3 Monograph (01/2009:2206; "Filgrastim Concentrated Solution", page 4143: "Impurities with charges differing from that of filgrastim. Isoelectric focusing (2.2.54)") except that reference solutions with a lower concentration and silver staining were used to achieve higher sensitivity.

Example 1

The following aqueous acetate or glutamate buffered compositions of filgrastim as a non-glycosylated recombinant human G-CSF were prepared as shown in Table 1 below and used in the following experiments:

TABLE 1

| Composition | G-CSF (mg/ml) | Buffer (10 mM) | Sorbitol | pH |
| --- | --- | --- | --- | --- |
| 1 | 2.26 | Acetate | 50 mM | 4.1 |
| 2 | 1.90 | Glutamate | 50 mM | 4.4 |
| 3 | 3.10 | Acetate | 50 mM | 4.5 |
| 4 | 3.30 | Acetate | 50 mM | 4.5 |
| 5 | 1.98 | Glutamate | 50 mM | 4.4 |
| 6 | 1.86 | Glutamate | 50 mM | 4.4 |
| 7 | 1.70 | Glutamate | 50 mM | 4.4 |
| 8 | 1.79 | Glutamate | 50 mM | 4.4 |

The G-CSF content in mg/ml of each composition was defined to be the 100% value in all following experiments.

Example 2

Compositions 1 and 2 (30 ml in a polyethylene (PE) bag) were subjected to freezing and thawing under various conditions using the Integrated Biosystems CryoPilot™ System. Percentages of aggregates, oligomers, dimers and monomers of G-CSF as well as overall G-CSF content were determined using SEC as described in the European Pharmacopoeia 6.3 Monograph (01/2009:2206; "Filgrastim Concentrated Solution", page 4143: "Impurities with molecular masses higher than that of filgrastim. Size-exclusion chromatography (2.2.30)"). All values were determined before freezing (T0) and after freezing and thawing following conditions A, B and C. Results and Freeze/Thaw (F/T) conditions are indicated in Table 2 below.

TABLE 2

| Composition | F/T conditions | Aggregate (%) | Oligomers (%) | Dimers (%) | Monomers (%) | G-CSF content (%) |
|---|---|---|---|---|---|---|
| 1 | T0 | <0.1 | <0.1 | 0.3 | 99.7 | 100.2 |
|   | A  | <0.1 | <0.1 | 0.4 | 99.6 | 85.0  |
|   | B  | <0.1 | <0.1 | 0.4 | 99.5 | 98.7  |
|   | C  | <0.1 | <0.1 | 0.4 | 99.5 | 102.9 |
| 2 | T0 | <0.1 | <0.1 | 0.2 | 99.8 | 100.0 |
|   | A  | <0.1 | <0.1 | 0.3 | 99.7 | 74.3  |
|   | B  | <0.1 | <0.1 | 0.4 | 99.6 | 100.6 |
|   | C  | <0.1 | <0.1 | 0.4 | 99.6 | 100.8 |

F/T Conditions:

T0: Compositions before freezing

A: Compositions were quickly cooled to −20° C. Following storage of the compositions at this temperature for 4 hs, the frozen compositions were immediately transferred to a temperature of +20° C. Compositions were kept for 2 hs at that temperature and then were transferred to a temperature of +4° C. where they were kept for further 12 hs. Compositions had completely thawed after 2 hs at +20° C. and 1 h at 4° C.

B: Compositions were quickly cooled from +4° C. to −20° C. Following storage for 4 hs at that temperature, temperature was slowly increased to a temperature of +4° C. over a period of 7 hs using the programmed CryoPilot™ linear temperature gradient.

C: Compositions were cooled from +4° C. to −20° C. over a period of 17 hs using the programmed CryoPilot™ linear temperature gradient. Thereafter, temperature was slowly raised to a temperature of +4° C. over a period of 7 hs using a programmed temperature gradient of the CryoPilot™ system.

The results show that quick thawing under condition A results in a significant loss of G-CSF content, while slowly increasing the temperature of the frozen compositions as under conditions B and C from −20° C. to +4° C. allows to obtain liquid compositions having a G-CSF content comparable to the G-CSF content of the originally provided G-CSF composition. Freezing rate has no effect on the final G-CSF content.

Example 3

Compositions 3 and 4 (3.5 ml in 5 ml PETG bottles) were subjected to 5 consecutive F/T cycles. In each cycle, samples were cooled from +4° C. to −20° C. in a freezer and after storage for 20 hours at −20° C. were directly transferred to a cold room adjusted to a temperature of +4° C. Samples were left at that temperature for a period of 16 hs for thawing and allowing the compositions to regain their original content in G-CSF. G-CSF content and impurities were determined at the beginning of the experiment and after cycle 1, 3 and 5 using SEC (multimers of filgrastim) and RP-HPLC (G-CSF content and deamidated and oxidized G-CSF variants) as described above. The results are shown in Table 3 below.

TABLE 3

| | | RP-HPLC | | | SEC |
|---|---|---|---|---|---|
| Composition | F/T cycle | G-CSF Content (%) | G-CSF Content (mg/ml) | Sum impurities (%) | Sum impurities (%) |
| 3 | 0 | 100 | 3.1 | 1.5 | 1.5 |
|   | 1 | 100 | 3.1 | 1.5 | 1.7 |
|   | 3 | 100 | 3.1 | 1.5 | 1.8 |
|   | 5 | 100 | 3.1 | 1.6 | 1.8 |
| 4 | 0 | 100 | 3.3 | 1.2 | 2.5 |
|   | 1 | 103 | 3.4 | 1.3 | 2.6 |
|   | 3 | 103 | 3.4 | 1.5 | 2.7 |
|   | 5 | 103 | 3.4 | 1.5 | 2.7 |

As may be seen from the above results, the G-CSF content as well as the sum of impurities remain essentially the same after each cycle, all values being within the limits of experimental error.

Example 4

Compositions 5 and 6 (7 ml in 10 ml PETG bottles) were cooled from +4° C. to −20° C. in a freezer. Frozen samples were stored for two months at −20° C. and then directly transferred to a cold room adjusted to a temperature of +4° C. Samples were left at that temperature for a period of 24 hs for thawing and allowing the compositions to regain their original content in G-CSF. For the time of the experiment, samples of compositions 5 and 6 were kept at 25° C. as a control.

All samples were analyzed for impurities with charges differing from that of filgrastim using Isoelectric Focussing (IEF) as described above. The results are shown in FIG. 1, wherein the principal band, i.e., the most intense band, represents filgrastim, and bands having lower intensities migrating below the main band represent mainly deamidated variants thereof. As will be seen from FIG. 1, samples stored at −20° C. (lanes 1 and 2) show considerably less deamidated variants of filgrastim than samples stored at 25° C. (lanes 3 and 4).

Furthermore, overall G-CSF content and impurities of the samples stored at −20° C. were determined using RP-HPLC (G-CSF content and deamidated and oxidized G-CSF variants) and SEC (multimers of G-CSF) as described above before freezing (T0) and following storage for two months and thawing (T1/−20° C.). The results are shown in Table 4 below together with the results for the control samples stored at 25° C. (T1/+25° C.).

TABLE 4

| | | RP-HPLC | | | SEC |
|---|---|---|---|---|---|
| Composition | Time of Testing | G-CSF Content (%) | G-CSF Content (mg/ml) | Sum impurities (%) | Sum impurities (%) |
| 5 | T0 | 100 | 1.98 | 1.5 | 0.2 |
|   | T1/−20° C. | 100 | 1.98 | 1.5 | 0.4 |
|   | T1/+25° C. | 100 | 1.98 | 2.9 | 0.1 |
| 6 | T0 | 100 | 1.86 | 2.6 | 0.2 |
|   | T1/−20° C. | 99 | 1.85 | 2.1 | 0.4 |
|   | T1/+25° C. | 99 | 1.84 | 3.6 | 0.1 |

As may be seen from the above results, the G-CSF content remains essentially the same before and after freezing, all values being within the limits of experimental error. The increase in deamidated and oxidized G-CSF variants as determined by RP-HPLC is in conformity with the results obtained using IEF shown in FIG. 1.

Example 5

Compositions 5, 7 and 8 (800 ml in 1000 ml PETG bottles) were stored for 36 months at −20° C. Following storage, the compositions were transferred to a cold room adjusted to a temperature of +4° C. and left at that temperature for thawing for a period of 48 hours. The liquid compositions thus obtained were subjected to 5 consecutive F/T cycles. In each cycle, samples were cooled from +4° C. to −20° C. in a freezer and after storing for at least 24 hours at −20° C. were directly transferred to a cold room adjusted to a temperature of +4° C. Samples were left at that temperature for a period of at least 48 hs for thawing and allowing the compositions to regain their original content in G-CSF. G-CSF content and impurities were determined at the beginning of the experiment (F/T0) and after completion of cycle 5 (F/T5) using RP-HPLC (G-CSF content and deamidated and oxidized G-CSF variants) and SEC (multimers of G-CSF) as described above. The results are shown in Table 5 below.

TABLE 5

| Composition | F/T cycle | RP-HPLC G-CSF Content (%) | RP-HPLC G-CSF Content (mg/ml) | RP-HPLC Sum impurities (%) | SEC Sum impurities (%) |
|---|---|---|---|---|---|
| 5 | 0 | 100 | 1.98 | 1.5 | 0.3 |
|   | 5 | 99  | 1.96 | 1.2 | 0.3 |
| 7 | 0 | 100 | 1.7  | 2.7 | 0.3 |
|   | 5 | 102 | 1.73 | 2.5 | 0.3 |
| 8 | 0 | 100 | 1.79 | 2.6 | 0.3 |
|   | 5 | 102 | 1.82 | 2.3 | 0.3 |

As may be seen from the above results, the G-CSF content as well as the sum of impurities before freezing and after completion of cycle 5 remain essentially the same, all values being within the limits of experimental error.

The invention claimed is:

1. A method for stable long-term storage of non-glycosylated recombinant human Granulocyte-Colony Stimulating Factor (G-CSF), said method comprising the steps of:
   (a) providing an aqueous acetate or glutamate buffered G-CSF composition containing a non-glycosylated recombinant human G-CSF and sorbitol, wherein the amount of G-CSF is in the range of from 0.1 mg/ml to 8.0 mg/ml and wherein said composition has a volume of from 100 ml to 8 l;
   (b) cooling the G-CSF-formulation provided in step (a) to a temperature of −15° C. or below to obtain a frozen G-CSF formulation;
   (c) storing the G-CSF-formulation obtained in step (b) in the frozen state over a period of at least one month;
   (d) increasing the temperature of the frozen G-CSF composition of step (c) to a temperature within the range of from 2° C. to 8° C. over a period of time of at least 6 hours to allow the composition to thaw and to obtain a liquid composition having a G-CSF content of at least 95% of the G-CSF content of the composition provided in step (a).

2. The method of claim 1, wherein the amount of G-CSF in the buffered G-CSF formulation of step (a) is in the range of from 0.25 mg/ml to 6.5 mg/ml.

3. The method of claim 1, wherein the buffered G-CSF composition has a pH of from 3.5 to 5.

4. The method of claim 1, wherein the acetate or glutamate concentration of the buffered G-CSF composition is in the range of from 0.5 mM to 100 mM.

5. The method of claim 1, wherein the amount of sorbitol in the G-CSF composition is in the range of from 10 to 100 mg/ml.

6. The method of claim 1, wherein the aqueous acetate or glutamate buffered G-CSF composition provided in step (a) has a volume of from 100 ml to 4 l.

7. The method of claim 1, wherein the G-CSF composition in step (b) is cooled to a temperature of between −15° C. and −25° C. or a temperature of between −60° C. and −80° C.

8. The method of claim 1, wherein the frozen G-CSF composition in step (c) is stored over a period of at least three months.

9. The method of claim 1, wherein temperature increase of the frozen G-CSF composition to a temperature within the range of from 2° C. to 8° C. in step (d) is effected by gradually or linearly increasing temperature over a period of time of at least 6 hours.

10. The method of claim 1, wherein temperature increase of the frozen G-CSF composition to a temperature in step (d) is effected by transferring the frozen composition to a temperature within the range of from 2° C. to 8° C. and maintaining the composition at said temperature for a period of time of at least 12 hours.

11. The method of claim 1, wherein the G-CSF composition is free of surfactant.

12. The method of claim 1, wherein the G-CSF composition comprises a surfactant.

13. A method of providing a pharmaceutical composition of non-glycosylated recombinant human G-CSF, said method comprising the steps of:
   (a) formulating non-glycosylated recombinant human G-CSF with an acetate or glutamate buffer and sorbitol to obtain an aqueous buffered G-CSF composition, wherein the amount of G-CSF is in the range of from 0.1 mg/ml to 8.0 mg/ml and wherein said composition has a volume of from 100 ml to 8 l;
   (b) cooling the G-CSF composition of step (a) to a temperature of −15° C. or below to obtain a frozen G-CSF composition;
   (c) storing the G-CSF composition obtained in step (b) in the frozen state over a period of at least one month;
   (d) increasing the temperature of the frozen G-CSF composition of step (c) to a temperature within the range of from 2° C. to 8° C. over a period of time of at least 6 hours to allow the composition to thaw and to obtain a liquid composition having a G-CSF content of at least 95% of the G-CSF content of the composition provided in step (a); and
   (e) filling the liquid composition obtained in step (d) into primary packagings for parenteral use.

* * * * *